US007161050B2

(12) United States Patent
Sherman et al.

(10) Patent No.: US 7,161,050 B2
(45) Date of Patent: *Jan. 9, 2007

(54) METHOD AND APPARATUS FOR SYNTHESIZING OLEFINS, ALCOHOLS, ETHERS, AND ALDEHYDES (75) Inventors: Jeffrey H. Sherman, Sebastian, FL (US); Eric W. McFarland, Santa Barbara, CA (US); Michael J. Weiss, Santa Barbara, CA (US); Ivan Marc Lorkovic, Santa Barbara, CA (US); Leroy E. Laverman, Santa Barbara, CA (US); Shouli Sun, Santa Barbara, CA (US); Dieter J. Schaefer, Goleta, CA (US); Galen Stucky, Goleta, CA (US); Peter Ford, Santa Barbara, CA (US)

(73) Assignees: GRT, Inc., Oakland, CA (US); The Regents of the University of California, Oakland, CA (US)

( * ) Notice: Subject to any disclaimer, the term of this patent is extended or adjusted under 35 U.S.C. 154(b) by 451 days.

This patent is subject to a terminal disclaimer.

(21) Appl. No.: 10/430,240

(22) Filed: Aug. 19, 2003

(65) Prior Publication Data

US 2004/0006246 A1 Jan. 8, 2004

Related U.S. Application Data (63) Continuation-in-part of application No. 10/365,346, filed on Feb. 12, 2003, which is a continuation of application No. 10/298,440, filed on Nov. 20, 2002, now abandoned, which is a continuation-in-part of application No. 10/208,068, filed on Jul. 29, 2002, now abandoned, which is a continuation-in-part of application No. 10/054,004, filed on Jan. 24, 2002, now Pat. No. 6,486,368, which is a continuation-in-part of application No. 09/951,739, filed on Sep. 11, 2001, now Pat. No. 6,465,696, which is a continuation-in-part of application No. 09/886,078, filed on Jun. 20, 2001, now Pat. No. 6,472,572.

(51) Int. Cl.
  $C07C\ 5/00$ (2006.01)
  $C07C\ 47/27$ (2006.01)
  $C07C\ 45/00$ (2006.01)
  $C07C\ 47/02$ (2006.01)
  $C07C\ 29/62$ (2006.01)

(52) U.S. Cl. .................. 585/324; 585/318; 585/501; 568/490; 568/448; 568/449; 568/893; 568/671; 568/891; 568/910

(58) Field of Classification Search ............... 585/324, 585/318, 501; 568/490, 448, 449, 893, 671, 568/891, 910
See application file for complete search history.

(56) References Cited

U.S. PATENT DOCUMENTS

| 3,172,915 | A | 3/1965 | Borkowski |
| 3,273,964 | A | 9/1966 | Rosset |
| 3,310,380 | A | 3/1967 | Lester |
| 3,353,916 | A | 11/1967 | Lester ........................ 23/216 |
| 3,894,107 | A | 7/1975 | Butter et al. ................ 260/668 |
| 4,006,169 | A | 2/1977 | Anderson et al. ........... 260/348 |
| 4,301,253 | A | 11/1981 | Warren ....................... 518/700 |
| 4,333,852 | A | 6/1982 | Warren ....................... 252/429 |
| 4,373,109 | A | 2/1983 | Olah .......................... 585/640 |
| 4,440,871 | A | 4/1984 | Lok et al. ................... 502/214 |
| 4,465,893 | A | 8/1984 | Olah .......................... 585/709 |
| 4,496,752 | A | 1/1985 | Gelbein et al. ............. 549/521 |
| 4,513,092 | A | 4/1985 | Chu et al. .................... 502/71 |
| 4,523,040 | A | 6/1985 | Olah .......................... 568/671 |
| 4,654,449 | A | 3/1987 | Chang et al. ............... 570/261 |
| 4,769,504 | A | 9/1988 | Noceti et al. ............... 585/415 |
| 4,795,843 | A | 1/1989 | Imai et al. .................. 585/408 |
| 4,982,024 | A | 1/1991 | Lin et al. ..................... 570/262 |
| 5,087,786 | A | 2/1992 | Nubel et al. ................ 585/500 |
| 5,243,098 | A | 9/1993 | Miller et al. ................ 568/893 |
| 5,276,240 | A | 1/1994 | Timmons et al. |
| 5,334,777 | A | 8/1994 | Miller et al. ................ 568/859 |
| 5,486,627 | A | 1/1996 | Quarderer, Jr. et al. ..... 549/521 |
| 5,998,679 | A | 12/1999 | Miller ......................... 568/859 |
| 6,403,840 | B1 | 6/2002 | Zhou et al. ................. 568/579 |
| 6,452,058 | B1 | 9/2002 | Schweizer et al. .......... 570/223 |
| 6,462,243 | B1 | 10/2002 | Zhou et al. ................. 568/893 |
| 6,465,696 | B1 | 10/2002 | Zhou et al. ................. 568/671 |
| 6,465,699 | B1 | 10/2002 | Grosso ....................... 568/893 |
| 6,472,572 | B1 | 10/2002 | Zhou et al. ................. 568/893 |

(Continued)

FOREIGN PATENT DOCUMENTS

BR         0210054         8/2004

(Continued)

OTHER PUBLICATIONS

The Catalytic Dehydrohalogenation of Haloethanes on Solid Acids and Bases, Mochida, et al., Bulletin of the Chemical Society of Japan, vol. 44, 3305-3310, 1971.

(Continued)

Primary Examiner—Elvis O. Price
(74) Attorney, Agent, or Firm—Christie, Parker & Hale LLP.

(57) ABSTRACT

A reactant selected from the group consisting of alkanes, alkenes, alkynes, dienes, and aromatics is reacted with a halide selected from the group including chlorine, bromine, and iodine to form a first reaction product. The first reaction product is reacted with a solid oxidizer to form a product selected from the group including olefins, alcohols, ethers, and aldehydes, and spent oxidizer. The spent oxidizer is oxidized to form the original solid oxidizer and the second reactant which are recycled.

26 Claims, 4 Drawing Sheets

U.S. PATENT DOCUMENTS

| | | | |
|---|---|---|---|
| 6,486,368 B1 | 11/2002 | Zhou et al. | 568/893 |
| 6,525,230 B1 | 2/2003 | Grosso | 568/891 |
| 6,713,087 B1 | 3/2004 | Tracy et al. | 424/486 |
| 2002/0198416 A1 | 12/2002 | Zhou et al. | 568/910 |
| 2003/0069452 A1 | 4/2003 | Sherman et al. | 568/694 |
| 2003/0078456 A1 | 4/2003 | Yilmaz et al. | 568/488 |
| 2003/0120121 A1 | 6/2003 | Sherman et al. | 568/800 |
| 2003/0125583 A1 | 7/2003 | Yilmaz et al. | 568/490 |
| 2003/0166973 A1 | 9/2003 | Zhou et al. | 568/488 |
| 2004/0006246 A1 | 1/2004 | Sherman et al. | 568/470 |

FOREIGN PATENT DOCUMENTS

| | | |
|---|---|---|
| CA | 2447761 | 11/2002 |
| CA | 2471295 | 7/2003 |
| EP | 1395536 | 3/2004 |
| EP | 1404636 | 4/2004 |
| EP | 1435349 | 7/2004 |
| EP | 1474371 | 11/2004 |
| JP | 2004-529189 | 9/2004 |
| WO | PCT/US99/17980 | 8/1999 |
| WO | WO00/007718 | 2/2000 |
| WO | WO 00/07718 | 2/2000 |
| WO | WO 00/09261 | 2/2000 |
| WO | WO00/09261 | 2/2000 |
| WO | WO 02/094751 | 11/2002 |
| WO | WO 03/000635 | 1/2003 |
| WO | WO 03/022827 | 3/2003 |
| WO | WO 03/062172 | 7/2003 |

OTHER PUBLICATIONS

Nanocrystalline Ultra High Surface Area Magnesium Oxide as a Selective Base Catalyst, Ryan Richards, et al., Scripta Materialia. 44 (2001) 1663-1666.

Nanocrystal Metal Oxide—Chlorine Adducts: Selective Catalysts for Chlorination of Alkanes, Naijian Sun and Kenneth J. Klabunde, J. Am. Chem. Soc., 1999, 121, 5587-5588.

Nanocrystalline MgO as a Dehydrohalogenation Catalyst, Ilya V. Mishakov, et al., Journal of Catalysis 206, 40-48 (2002).

Reactions of VX, GD, and HD with Nanosize CaO: Autocatalytic Dehydrohalogenation of HD, George W. Wagner, et al., J. Phys. Chem. B. 2000, 104, 5118-5123.

Ionic Bromination of Ethane and Other Alkanes (Cycloaklanes) with Bromine Catalyzed by the Polyhalomethane 2AlBr3 Aprotic Organic Superacids under Mild Conditions; Irena S. Akhren, et al.; Tetrahedron Letters, vol. 36, No. 51, pp. 9365-9368, 1995.

Selective bromination of alkanes and arylaklanes with CBr4; Vladimir V. Smirnov, et al., Mendeleev Communications Electronic Version, Issue 5, 2000 (pp. 167-206).

Selective Monohalogenation of Methane over Supported Acid or Platinum Metal Catalysts and Hydrolysis of Methyl Halides over y-Alumina-Supported Metal Oxide/Hydroxide Catalysts. A Feasible Path for the Oxidative Conversion of Methane into Methyl Alcohol/ Dimethyl Ether; George B. Olah, et al.; Contribution from the Donald P. and Katherine B. Locker Hydrocarbon Research Institute and Department of Chemistry, University of Southern California, Los Angeles, CA; received Apr. 22, 1985.

Electrophilic Methane Conversion; by George A. Olah; Acc. Chem. Res. 1987, 20, 422-428, Loker Hydrocarbon Research Institute and Department of Chemistry, University of Southern California, Los Angeles, CA.

Antimony Pentafluoride/Graphite Catalyzed Oxidative Carbonylation of Methyl Halides with Carbon Monoxide and Copp Oxides (or Copper/Oxygen) to Methyl Acetate; by George A. Olah and Jozef Bukala; J. Org. Chem., 1990, 55, 4293-4297; Donald P. and Katherine B. Loker Hydrocarbon Research Institute and Department of Chemistry, University of Southern California, University Park, Los Angeles, CA.

Superacid-Catalyzed Carbonylatio of Methane, Methyl Halides, Methyl Alcohol, and Dimethyl Ether to Methyl Acetate a Acetic Acide; by Alessandro Bagno, Jozef Bukala, and George A. Olah; J. Org. Chem. 1990, 55, 4284-4289; Donald P. and Katherine B. Loker Hydrocarbon Research Institute, University of Southern California, University Park, Los Angeles, CA.

The Catalytic Dehydrohalogenation of Haloethanes on Solid Acids and Bases, Mochida, et al., Bulletin of the Chemical Society of Japan, vol. 44, 3305-3310, 1971.

Nanocrystalline Ultra High Surface Area Magnesium Oxide as a Selective Base Catalyst, Ryan Richards, et al., Scripta Materialia, 44, 2001, pp. 1663-1666.

Nanocrystal Metal Oxide- Chlorine Adducts: Selective Catalysts for Chlorination of Alkanes, Naijian Sun and Kenneth J. Klabunde, J. Am. Chem. Soc., 1999, 121, 5587-5588.

Nanocrystalline MgO as a Dehydrohalogenation Catalyst, Ilya V. Mishakov, et al., Journal of Catalysis 206, 40-48, 2002.

Reactions of VX, GD, and HD with Nanosize CaO: Autocatalytic Dehydrohalogenation of HD, George W. Wagner, et al., J. Phys. Chem. B. 2000, 104, 5118-5123.

Changes in Texture and Catalytic Activity of Nanocrystalline MgO during Its Transformation to MgCl2 in the Reaction with 1-Chlorobutane, Kenneth J. Klabunde, et al., J. Phys. Chem. B. 2001, 105, 3937-3941.

Ionic Bromination of Ethane and Other Alkanes (Cycloalkanes) with Bromine Catalyzed by the Polyhalomethane 2AlBr3 Aprotic Organic Superacids under Mild Conditions; Irena S. Akhren, et al.; Tetrahedron Letters, vol. 36, No. 51, pp. 9365-9368,1995.

Selective bromination of alkanes and arylalkanes with CBr4; Vladimir V. Smirnov, et al., Mendeleev Communications Electronic Version, Issue 5, 2000 (pp. 167-206).

Selective Monohalogenation of Methane over Supported Acid or Platinum Metal Catalysts and Hydrolysis of Methyl Halides over y-Alumina-Supported Metal Oxide/Hydroxide Catalysts. A Feasible Path for the Oxidative Conversion of Methane into Methyl Alcohol/ Dimethyl Ether; George B. Olah, et al.; Contribution from the Donald P. and Katherine B. Loker Hydrocarbon Research Institute and Department of Chemistry, University of Southern California, Los Angeles, CA; received Apr. 22, 1985 (J. Am. Chem. Soc. 1985, 107, 7097-7105).

Electrophilic Methane Conversion; by George A. Olah; Acc. Chem. Res. 1987, 20, 422-428, Loker Hydrocarbon Research Institute and Department of Chemistry, University of Southern California, Los Angeles, California.

Antimony Pentafluoride/Graphite Catalyzed Oxidative Carbonylation of Methyl Halides with Carbon Monoxide and Copper Oxides (or Copper/Oxygen) to Methyl Acetate; by George A. Olah and Jozef Bukala; J. Org. Chem., 1990, 55, No. 14, 4293-4297; Donald P. and Katherine B. Loker Hydrocarbon Research Institute and Department of Chemistry, University of Southern California, University Park, Los Angeles, California.

Superacid-Catalyzed Carbonylation of Methane, Methyl Halides, Methyl Alcohol, and Dimethyl Ether to Methyl Acetate a Acetic Acide; by Alessandro Bagno, Jozef Bukala, and George A. Olah; J. Org. Chem. 1990, vol. 55, No. 14, 4284-4292; Donald P. and Katherine B. Loker Hydrocarbon Research Institute, University of Southern California, University Park, Los Angeles, California.

Ylide chemistry. I. Bifunctional acid-base-catalyzed conversion of heterosubstituted methanes into ethylene and derived hydrocarbons. The onium-ylide mechanism of the C1→C2 conversion by George A. Olah et al. (J. Am. Chem. Soc. 106, 2143-2149 (1984)).

Grignard Reagents with Transition Metal Halides: Disproportionation, and Exchange with Olefins; by Masuhiko Tamura and Jay K. Kochi, Bulletin of the Chemical Society of Japan, v. 44, 1971 pp. 3063-3073.

The Catalytic Dehydrohalogenation of Haloethanes on Solid Acids and Bases, Mochida, et al., Bulletin of the Chemical Society of Japan, vol. 44, 3305-3310, 1971.

Nanocrystalline Ultra High Surface Area Magnesium Oxide as a Selective Base Catalyst, Ryan Richards, et al., Scripta Materialia, 44, 2001, pp. 1663-1666.

Nanocrystal Metal Oxide-Chlorine Adducts: Selective Catalysts for Chlorination of Alkanes, Naijian Sun and Kenneth J. Klabunde, J. Am. Chem. Soc., 1999, 121, 5587-5588.

Nanocrystalline MgO as a Dehydrohalogenation Catalyst, Iiya V. Mishakov, et al., Journal of Catalysis 206, 40-48, 2002.

Reactions of VX, GD, and HD with Nanosize CaO: Autocatalytic Dehydrohalogenation of HD, George W. Wagner, et al., J. Phys. Chem. B. 2000, 104, 5118-5123.

Changes in Texture and Catalytic Activity of Nanocrystalline MgO during Its Transformation to $MgCl_2$ in the Reaction with I-Chlorobutane, Kenneth J. Klabunde, et al., J. Phys. Chem. B. 2001, 105, 3937-3941.

http://webbook.nist.gov/.

Monomethyl-Branching of Long n-Alkanes in the Range from Decane to Tetracosane on Pt/H-ZSM-22 Bifunctional Catalyst, Marion C. Claude and Johan A. Martens, Journal of Catalysts 190, pp. 39-48 (2000).

Synthesis and Characterization of a Catalytically Active Nickel-Silicoaluminophosphate Catalyst for the Conversion of Methanol to Ethene; J.M. Thomas, Y Xu, C.R.A. Catlow, and J.W. Couves; Chem. Mater. 1991, 3, 667-672.

Catalytically active centres in porous oxides: design and performance of highly selective new catalysts; John Meurig Thomas and Robert Raja; The Royal Society of Chemistry 2001, Chem. Commun., 2001, 675-687.

C1 Coupling via bromine activation and tandem catalytic condensation and neutralization over CaO/zeolite composites; Ivan Lorkovic, et al.; The Royal Society of Chemistry 2004; Chem. Commun. 2004, pp. 566-567.

Industrial Organic Chemistry; K. Weissermel and H.J. Arpo, 3rd ed., 1997, pp. 160-162, 208.

METHOD AND APPARATUS FOR SYNTHESIZING OLEFINS, ALCOHOLS, ETHERS, AND ALDEHYDES

CROSS-REFERENCE TO RELATED APPLICATIONS

This application is a continuation-in-part of prior application Ser. No. 10/365,346 filed Feb. 12, 2003, which is a continuation of prior application Ser. No. 10/298,440 filed Nov. 20, 2002, abandoned, which is a continuation-in-part of prior application Ser. No. 10/208,068, filed Jul. 29, 2002, abandoned, which is a continuation-in-part of prior application Ser. No. 10/054,004 filed Jan. 24, 2002, now U.S. Pat. No. 6,486,368, which is a continuation-in-part of prior application Ser. No. 09/951,739, filed Sep. 11, 2001, now U.S. Pat. No. 6,465,696, which is a continuation-in-part of application Ser. No. 09/886,078 filed Jun. 20, 2001, now U.S. Pat. No. 6,472,572.

TECHNICAL FIELD

This invention relates generally to methods and apparatus for synthesizing olefins, alcohols, ethers, and aldehydes from alkanes, alkenes, and aromatics, and more particularly to improvements in the selectivities of the reactions disclosed in the patents and patent applications identified herein, and to specific applications thereof.

BACKGROUND AND SUMMARY OF THE INVENTION

Application Ser. No. 10/208,068 filed Jun. 29, 2002, discloses a process for converting ethane to diethyl ether, ethanol and ethyl acetate wherein ethane reacts with a halogen selected from the group including chlorine, bromine, and iodine. For example, ethane is reacted with bromine to form bromoethane and HBr. The bromoethane then reacts with metal oxide to form diethyl ether, ethanol, ethyl acetate, and metal bromide. The metal bromide reacts with oxygen or air to regenerate the original metal oxide. In the process, bromine and metal oxide are recycled.

Application Ser. No. 10/365,346 filed Feb. 12, 2003 discloses a process wherein a reactant comprising an alkane, an alkene, or an aromatic is reacted with a metal halide to produce the halide of the reactant and reduced metal. The reduced metal is oxidized with air or oxygen to form the corresponding metal oxide. The metal oxide is reacted with the halide of the reactant to form the alcohol and/or the ether corresponding to the original alkane, alkene, or aromatic and the original metal halide which is recycled.

The present application comprises processes for synthesizing olefins, alcohols, ethers, and aldehydes which involve the use of solid phase catalysts/reactants in addition to the metal oxides and metal halides disclosed in the above-identified applications. The present application further comprises techniques for improving the selectivity of the reactions disclosed in previously filed applications which involve, for example, temperature control. The present application further comprises specific utilizations of the disclosed processes.

BRIEF DESCRIPTION OF THE DRAWINGS

A more complete understanding of the invention may be had by reference to the following Detailed Description when taken in conjunction with the accompanying Drawings wherein.

DETAILED DESCRIPTION

Figure 1:
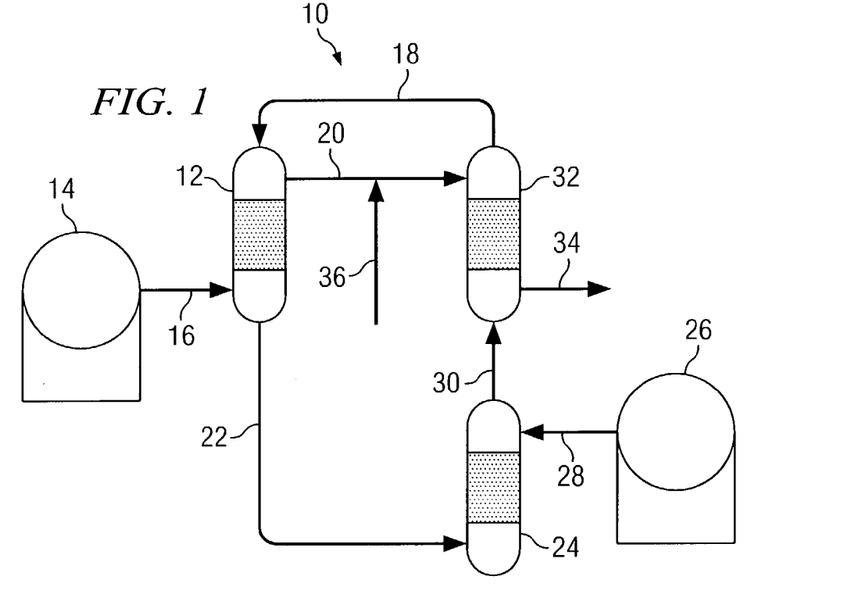
FIG. 1 is a diagrammatic illustration of a first embodiment of the invention.

Referring now to the Drawings, and particularly to FIG. 1 thereof, there is shown a method and apparatus 10 for synthesizing alcohols and/or ethers comprising a first embodiment of the invention. The method and apparatus 10, as well as the other embodiments of the invention hereinafter described, can be used to synthesize olefins, alcohols, ethers, and/or aldehydes. The following description wherein alcohols and/or ethers are synthesized from alkenes is representative.

A selected alkane, which may comprise methane, ethane, propane, butane, isobutane, pentane, hexane, cyclohexane, etc., is received in a first reactor 12 from a suitable source 14 through a line 16. The reactor 12 also receives a metal halide through a line 18. The halide comprising the metal halide that is received in the reactor 12 is selected from the group including chlorine, bromine, and iodine.

The reaction of the alkane with the metal halide produces the corresponding alkyl halide which is recovered through a line 20. The reaction also produces metal in reduced form, such as a metal hydride, which is recovered through a line 22 and directed to a second reactor 24. The second reactor 24 also receives oxygen and/or air from a source 26 through a line 28.

The second reactor 24 functions to convert the reduced metal received through the line 22 to metal oxide which is recovered through a line 30 and directed to a third reactor 32. The temperature of the reaction within the second reactor 24 is low enough that any bromine remaining on the metal following the reaction in the first reactor 12 remains on the metal, and only the hydrogen on the metal is replaced with oxygen. The hydrogen liberated from the metal is converted to water.

Within the third reactor 32 the alkyl halide formed in the first reactor 12 reacts with the metal oxide formed in the second reactor 24 to form the corresponding alcohol and/or ether which is recovered through an outlet 34. The reaction in the third reactor 32 also produces metal halide which is recycled to the first reactor 12 through the line 18.

In accordance with a specific application of the invention, the first reactor 12 receives ethane from the source 14 through the line 16, and the metal halide received in the reactor 12 through the line 18 comprises metal bromide. The reaction within the reactor 12 produces ethyl bromide which is recovered through the line 20 and directed to the third reactor 32. The reaction within the third reactor 32 may be characterized as follows:

$4CH_3CH_2Br + \text{Metal Oxide} + XH_2O \rightarrow 2CH_3CH_2OH + CH_3CH_2OCH_2CH_3 + \text{Metal Bromide}_2$ As will therefore be apparent, the reaction within the reactor 32 can be biased toward the production of alcohol or toward the production of ether depending upon the amount of water present within the reactor. FIG. 1 further illustrates an operational mode of the first embodiment of the invention whereby steam is directed into the line 20 through a line 36 and enters the reactor 32 with the ethyl bromide and the HBr that were produced in the reactor 12. As will be apparent from the formula set forth above, the introduction of steam into the reactor 32 causes the reaction therein to be selective toward the production of ethanol in the reactor 32 as opposed to the production of diethyl ether.

Figure 2:
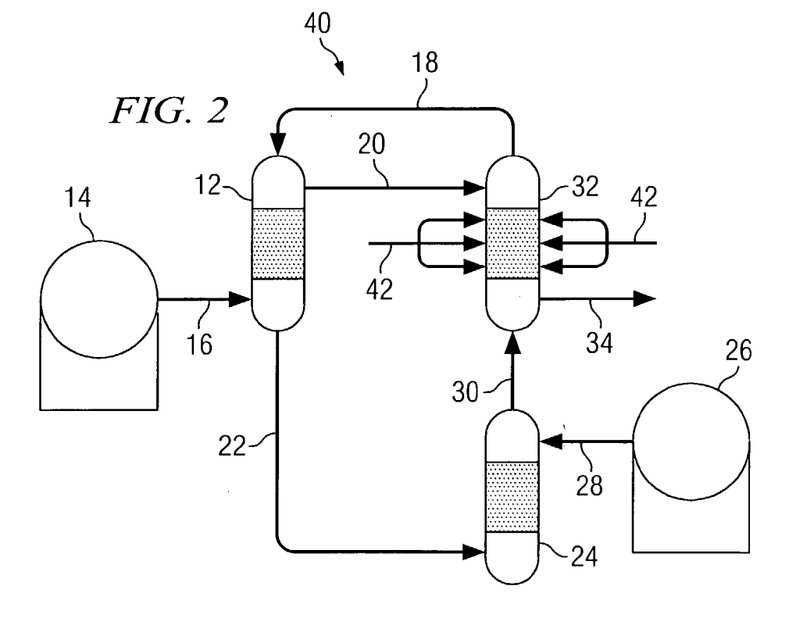
FIG. 2 is a diagrammatic illustration of a second embodiment of the invention.

Referring now to FIG. 2, there is shown a method of and apparatus for producing olefins, alcohols, ethers, and/or aldehydes comprising a second embodiment of the invention. Many of the components parts of the second embodiment of the invention are identical in construction and function to component parts of the first embodiment of the invention as illustrated in FIG. 1 and described hereinabove in conjunction therewith. Such identical component parts are designated in FIG. 2 with the same reference numerals utilized in the description of the first embodiment of the invention.

The second embodiment of the invention differs from the first embodiment of the invention in that rather than being directed into the reactor 32 through the line 20, steam is injected directly into the reactor 32 through lines 42. This allows the steam to be added to the reactor 32 at specific points in the reactor thereby increasing the selectivity of the reaction that takes place therein towards the production of alcohol and away from the production of ether.

Figure 3:
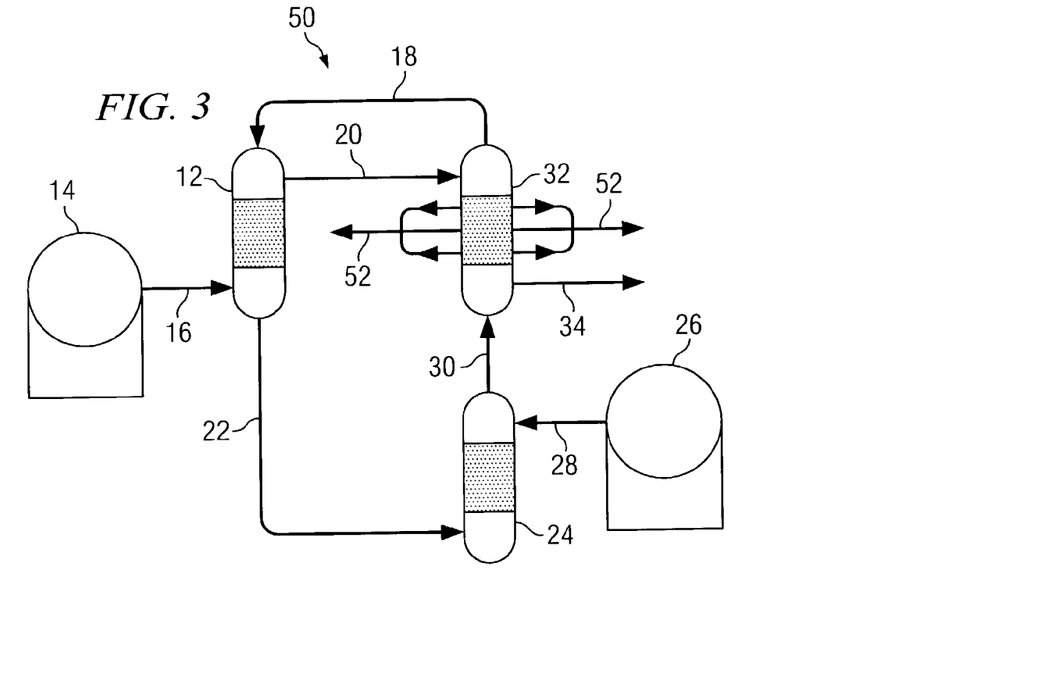
FIG. 3 is a diagrammatic illustration of a third embodiment of the invention.

A method and apparatus 50 for producing olefins, alcohols, ethers, and/or aldehydes comprising a third embodiment of the invention is illustrated in FIG. 3. Many of the component parts of the third embodiment of the invention are identical in construction and function to component parts of the first embodiment of the invention which are illustrated in FIG. 1 and described hereinabove in conjunction therewith. Such identical component parts are designed in FIG. 3 with the same reference numerals utilized in the description of the first embodiment of the invention.

The third embodiment of the invention differs from the first and second embodiments in that during the operation thereof water is removed from the reactor 32 through lines 52. The removal of water from the reactor 32 is accomplished by either distillation or by osmosis or by both. As will be apparent from the reaction set forth above, the removal of water from the reaction 32 causes the reaction that takes place therein to be selective toward the production of ether as opposed to the production of alcohol.

Figure 4:
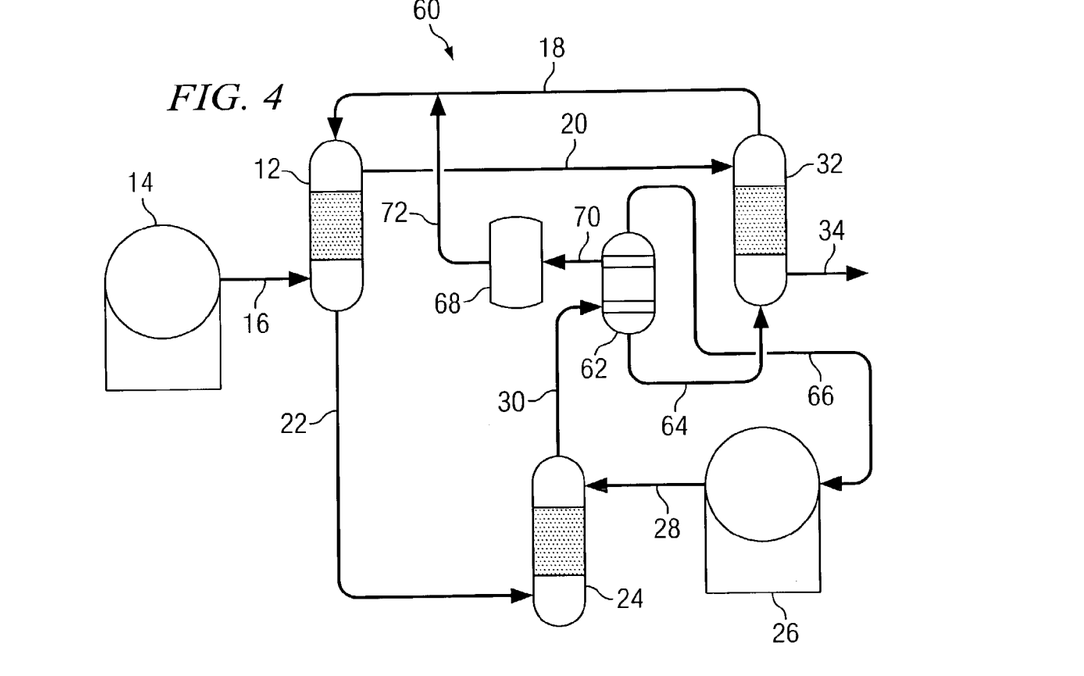
FIG. 4 is a diagrammatic illustration of a fourth embodiment of the invention.

Referring now to FIG. 4, there is shown a method and apparatus 60 for producing olefins, alcohols, ethers, and/or aldehydes comprising a fourth embodiment of the invention. Many of the component parts of the fourth embodiment of the invention are identical in construction and function to components of the first embodiment of the invention as illustrated in FIG. 1 and described hereinabove in conjunction therewith. Such identical components are designated in FIG. 4 with the same reference numerals utilized in the description of the first embodiment of the invention.

In accordance with the fourth embodiment of the invention, oxygen and/or air is directed into the second reactor 24 at a rate such that in addition to oxidizing the reduced metal back to metal oxide, additional oxygen is added to the metal oxide and molecular halide is liberated. The reaction products from the second reactor 34 are directed to a separator 62. The separator 62 directs metal oxide to the reactor 32 through a line 64, returns oxygen to the source 26 through a line 66 and directs halide to a halide storage tank 68 through a line 70. From the storage tank 68, the halide is directed to the reactor 12 through a line 72 and the line 18 thereby assuring an optimum level of halide within the reactor 12 at all times.

Figure 5:
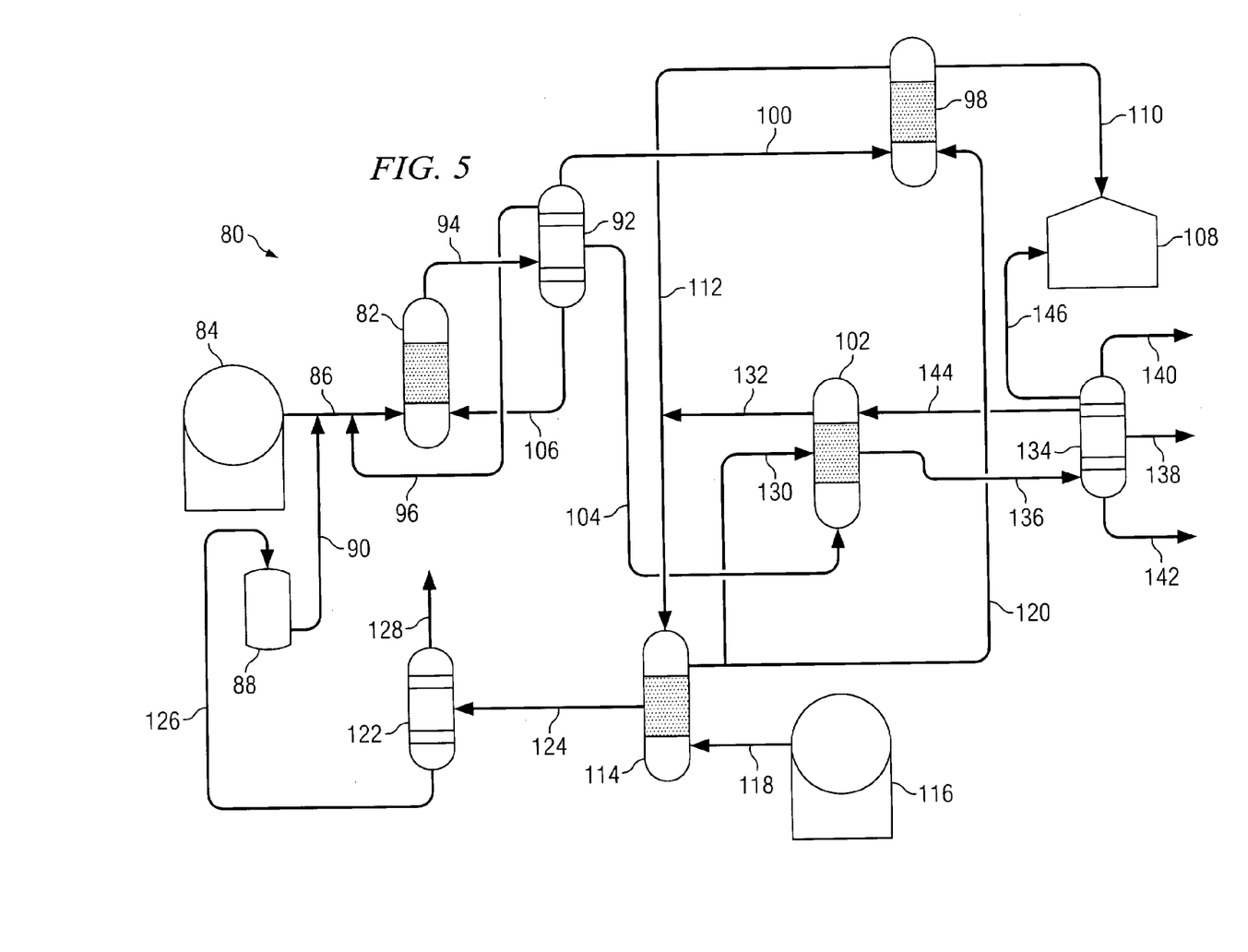
FIG. 5 is a diagrammatic illustration of a fifth embodiment of the invention.

Referring to FIG. 5, there is shown a method and apparatus 80 for producing olefins, alcohols, ethers and/or aldehydes comprising a fifth embodiment of the invention. The fifth embodiment of the invention is particularly useful in the production of olefins.

A selected alkane, which may comprise methane, ethane, propane, butane, isobutene, pentane, hexane, cyclohexane, etc., is received in a first reactor 82 from a suitable source 84 through a line 86. The reactor 82 also receives a halide from a storage container 88 through a line 90 and the line 86. The halide that is received in the reactor 82 is selected from the group consisting of chlorine, bromine, and iodine.

Reaction products resulting from the operation of the reactor 82 are directed to a distillation separator 92 through a line 94. Unreacted alkane is returned from the separator 92 to the reactor 82 through a line 96 and the line 86. Hydrogen halide is directed from the separator 92 to a second reactor 98 through a line 100. Monoalkyl halide is directed from the separator 92 to a third reactor 102 through a line 104. Higher halides are returned from the separator 92 to the reactor 82 through a line 106.

Within the second reactor 98 hydrogen halide received through the line 100 is reacted with a metal oxide to produce metal halide and water. Water is directed from the second reactor 98 to a waste water storage container 108 through a line 110. Metal halide, including the halide component of the hydrogen halide received in the reactor 98 through the line 100, is directed through a line 112 to a fourth reactor 114. The reactor 114 also receives air or oxygen from a suitable source 116 through a line 118. The reactor 114 produces regenerated oxide which is returned to the second reactor 98 through a line 120.

The fourth reactor 114 also produces halide, carbon dioxide, and water all of which are directed to a separator 122 through a line 124. The separator 122 removes the halide from the water and carbon dioxide, and directs the recovered halide to the halide storage container 88 through a line 126. Water and carbon dioxide are recovered from the separator 122 through a line 128.

In addition to receiving monoalkyl halide through the line 104, the third reactor 102 receives regenerated metal oxide through the line 120 and a line 130. The reaction within the third reactor 102 produces metal halide which is directed to the fourth reactor 114 through a line 132 and the line 112. The remaining reaction products resulting from operation of the third reactor 102 are directed to a distillation separator 134 through a line 136.

Operation of the distillation separator 134 produces the desired olefin which is recovered through a line 138. Light byproducts are recovered through a line 140, and heavy byproducts are recovered through a line 142. Unreacted monoalkyl halide is directed from the separator 134 to the third reactor 102 through a line 144. Water resulting from operation of the separator 134 is directed to the waste water container 108 through a line 146.

Figure 6:
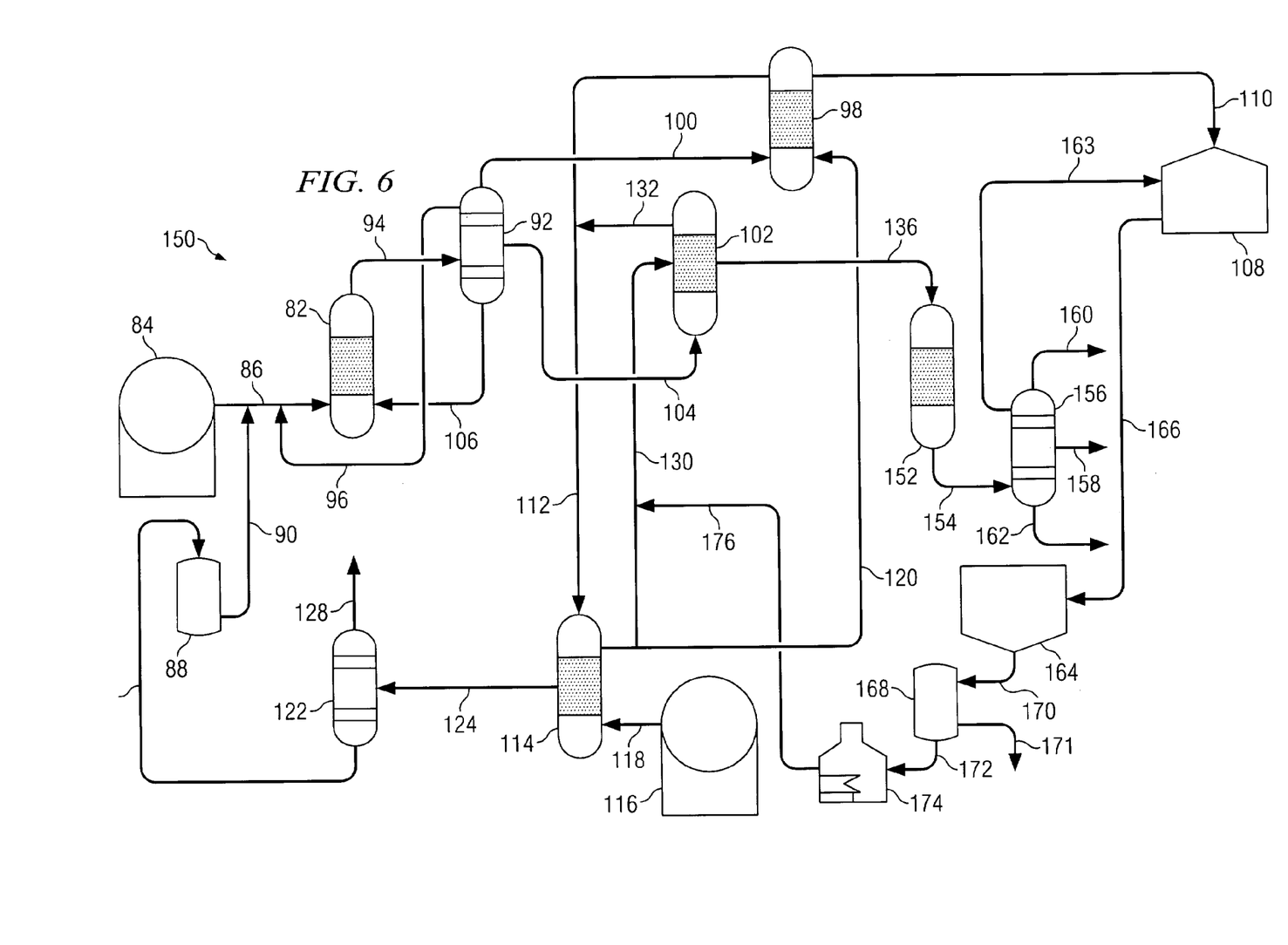
FIG. 6 is a diagrammatic illustration of a sixth embodiment of the invention.

Referring now to FIG. 6, there is shown a method of and apparatus for producing olefins, alcohols, ethers, and/or aldehydes comprising a sixth embodiment of the invention. Many of the component parts of the sixth embodiment of the invention are identical in construction and function to component parts of the fifth embodiment of the invention as illustrated in FIG. 5 and described hereinabove in conjunction therewith. Such identical component parts are designated in FIG. 6 with the same reference numerals utilized in the description of the fifth embodiment of the invention.

The sixth embodiment of the invention differs from the fifth embodiment thereof in that the reaction products resulting from operation of the third reactor 102 other than the metal halide are directed through the line 136 to a fifth reactor 152 which functions to convert the reaction products resulting from operation of the second reactor 102 to the corresponding alcohols. Reaction products resulting from operation of the fifth reactor 152 are directed through a line 154 to a distillation separator 156. The desired alcohol is recovered from the separator 156 through a line 158. Light byproducts are recovered through a line 160, and heavy byproducts are recovered through a line 162. Water resulting from operation of the separator 156 is directed to the waste water storage container 108 through a line 163.

The sixth embodiment of the invention further differs from the fifth embodiment of the invention in that waste water from the waste water storage container 108 is directed to a waste water treatment system 164 through a line 166. Treated waste water resulting from operation of the system 164 is directed to a separator 168 through a line 170. Treated waste water is recovered from the separator 168 through a line 171, and boiler feed water is recovered from the separator 168 through a line 172. The boiler feed water is directed to a boiler 174 which produces steam. Steam resulting from operation of the boiler 174 is directed to the second reactor 102 through a line 176 and the line 130.

In accordance with a seventh embodiment of the invention, it has been determined that in addition to the metal oxides and metal halides which have been disclosed as useful reactants for converting alkyl halide to product as well as in the reactive neutralization of hydrogen halide, metal hydroxides are useful for this purpose. Also, while metal halide is believed to be the product resulting from the metal oxide reaction, it is also possible that the product of the metal oxide reaction is a metal oxyhalide.

In accordance with an eighth embodiment of the invention, other species have proven useful as catalysts/reactants. For example, the composition of the solid reactant may take the form of a solid hydrate, such as a metal oxyhydrate or hydrates of halides, sulfides, carbonates, phosphates, phosphides, nitrides and nitrates.

In accordance with a ninth embodiment of the invention, it has been determined that hydrocarbons beyond methane, ethane and propane and chosen from the group including paraffinic and naphthenic hydrocarbons may also be used as feedstocks for the process. This determination expands the overall utility of the process to hydrocarbons up to about 16 in carbon number and is applicable to linear, branched and cyclic alkanes.

In accordance with a tenth embodiment of the invention, it has been determined that control over reaction selectivity and product composition can be specifically controlled by intentional variations in the composition and form (as directed by the synthetic route) of the solid metal oxide. Specifically, small variations in the atomic composition of the metal oxide (composed of one or several metal atoms) effects the reactivity and/or selectivity and different synthetic routes of the same compositions give rise to different reactivity and/or selectivity.

The reaction pressure and temperature are also controllable parameters useful in tuning the reaction towards specific products. For example, a metal oxide that produces predominantly alcohol at a temperature of about 250° C. can be switched to producing predominantly olefin by increasing the temperature of the metal oxide reaction to between about 350° C. and about 400° C. The increase in temperature results in the favoring of the beta-hydrogen elimination reaction over the hydroxylation. However, it is important to note that other mechanisms for the generation of the olefin are possible. Another benefit of increasing the reaction temperature is the realized increase in the rate of conversion of alkyl bromide resulting in a shorter reaction times and a smaller reactor.

Since the noted temperature effects have been observed for a wide variety of materials without a conclusive exception, this effect is broadly applicable across the periodic table. Sample materials include MgO, CaO, $FeMoO_x$, $FeWO_x$, $La_2O_3$, $Ca(OH)_2$, PbO, CuO, $Bi_2O_3$, $MgZrO_x$, ZnO. Most significant has been the example of a mixed cobalt zirconium oxide (stoichiometry $CoZrO_x$).

EXAMPLE I $CoZrO_x$

A sample is prepared by mixing equal amounts of a 0.5 M solution of cobalt nitrate and a 0.5 M solution of zirconium propoxide, followed by drying at 120° C., and an overnight calcination at 500° C.

Ethane is reacted with bromine in a molar ratio of approximately 10:1, giving ~94% (carbon) selectivity to ethyl bromide plus higher brominated species. HBr is also present. Passing this mixture over $CoZrO_x$ gives ethyl bromide conversion that increases with temperature. The respective brominated ethane conversions at 175° C., 200° C., 225° C., and 250° C. are approximately 41%, 56%, 69%, and 82%. A run at 350° C. using 80% less oxide provides a conversion of better than 90%. The ethylene selectivities (moles of ethylene/moles of all detected products) are approximately 1%, 7%, 20%, 34%, and 90% at 175° C., 200° C., 225° C., 250° C., 350° C. At 350° C. (excluding unreacted ethyl bromide) the product mix is approximately 90% ethylene, 5% carbon dioxide, 4% vinyl bromide, and 1% other (largely acetone).

EXAMPLE II $CoZrO_x$

When ethyl bromide (98+%) is passed over the $CoZrO_x$ described above in Example I at 350° C., the products detected in the vapor product stream are approximately 95% ethylene with the majority of the balance being carbon dioxide.

As a process variation, either the metal oxide (or halide or oxyhalide) can function as a catalyst to dehydrobrominate the ethyl bromide to ethylene and hydrogen halide with the hydrogen halide subsequently being neutralized.

In accordance with an eleventh embodiment of the invention, a metal hydroxide is the operative species in the metathesis reaction. Passing an alkyl halide over the metal hydroxide produces the corresponding alcohol. Subsequently, the resulting metal halide is regenerated with air/oxygen to convert the metal halide to metal oxide, which is then reacted with steam to regenerate the metal hydroxide. In accordance with a second part of the eleventh embodiment, the air/oxygen stream used to regenerate the metal oxide is mixed with a controlled amount of steam such that the metal hydroxide is produced without having to pass through a distinct metal oxide stage.

A twelfth embodiment of the invention concerns the ability of the process to selectively produce a series of oxidation products through a feedstock consisting of multiple hydrocarbons that greatly simplifies product production when compared with existing processes.

In a conventional olefins production facility, ethane or light naphtha is thermally "cracked" by heating the ethane or light naphtha to high temperature and contacting the feedstock with steam. The "cracking" process operates through a free radical mechanism and results in numerous products, including alkane hydrocarbons (such as ethane), alkene hydrocarbons (such as ethylene), alkyne hydrocarbons (such as acetylene), diene hydrocarbons (such as butadiene), aromatic hydrocarbons (such as benzene) and coke. Following the production of these products, numerous distillation steps, many of which operate cryogenically, are required to separate one product from another for use as feedstocks for other petrochemicals. As an example, the separation of ethylene from ethane through distillation is both capital and energy-intensive as the two compounds have boiling points very close to each other.

In contrast to the conventional process, the present invention produces olefins directly from their alkane precursor from either a single alkane feed component or a complex mixture. One means of operating the process is as follows. The alkane feed or feed mixture is contacted with halide to form the monohalogenated analog of the alkane feed or feed mixture. Following the halogenation reaction, the reaction mixture is passed over a solid metal oxide at a temperature from about 105° C. and about 150° C. whereby hydrogen halide produced in the halogenation reaction is converted to water, which is then removed from the remaining alkyl monohalides. The alkyl monohalides and remaining alkanes, having substantially different boiling points are then separated through distillation. One or more streams, each comprising an alkyl halide of predetermined carbon number, is then produced. In this way the difficult separation of alkanes from alkenes (e.g. ethane from ethylene) is avoided. Alternatively, the separation of excess alkanes may precede the conversion of hydrogen halide to water. Subsequently, each alkyl monohalide may then be directed over a metal oxide at a temperature of between about 250° C. and about 350° C. to produce the olefin with corresponding carbon number to the alkyl monohalide.

Alternatively, the products of the halogenation reaction following the neutralization of the hydrogen halide and removal of the generated water can be directed as a group over a metal oxide and converted to the corresponding olefins. Following the generation of the olefins, the olefins can be separated as desired into one or more olefin product stream(s).

If the desired product of a specific alkane is an alcohol, an ether or an aldehyde, the present invention is especially useful. In the production of alcohols, ethers or aldehydes, the process can be operated in the exact fashion as described above for olefins up through the point where the alkyl monohalides are separated from each other. To produce an alcohol, an ether or an aldehyde from a specific alkyl monohalide, a specific alkyl monohalide is passed over a specific metal oxide that is selected based upon its selectivity to produce the desired functionality (i.e. alcohol, ether or aldehyde). Should the desired product selectivity be affected by the amount of water present in the reaction between the alkyl monohalide and the metal oxide, water can be added to the alkyl monobromide feed to the appropriate level. For example, water produced in the neutralization of hydrogen halide may be used for this purpose.

If it is desired to produce a stream of mixed alcohols, ethers or aldehydes, the present invention may do so by simply eliminating the step whereby the alkyl monohalides are separated from each other prior to the step of contacting the alkyl monohalide with a specific metal oxide. Rather to produce the mixed stream, the combined alkyl monohalides are simply passed as a group over the specific metal oxide and the desired mixed stream results. The mixed stream may then be utilized as is or separated as desired into one or more isolated product streams.

A thirteenth embodiment of the present invention comprises a method of retrofitting an existing olefins production facility to increase its capacity and reduce its operating cost. This invention builds upon the processes disclosed U.S. Pat. Nos. 6,462,243, 6,472,572, 6,486,368, and 6,465,696 to provide selective partial oxidation of alkanes, and involves the linking of the process disclosed therein to an existing olefins plant in such a way as to increase capacity with relatively minimal additional investment.

As a general approach to the retrofit embodiment, following the halogenation of an alkane stream, hydrogen halide is neutralized over a metal oxide as previously described. However, rather than separate the alkyl monobromides from each other, the entire stream of mixed alkyl monobromides is passed over a metal oxide and converted to a mixed stream of olefins. The resulting olefin stream is then directed into the plant's existing separation equipment along with material produced from the thermal cracking portion of the plant and is separated into specific olefin streams. As a more specific example of the retrofit embodiment, in a conventional ethylene facility, ethane or naphtha is cracked with rather poor selectivity and conversion to ethylene. In the process, a substantial ethane recycle stream is generated. The retrofit of the present invention involves capturing all or part of the ethane ordinarily recycled to the furnace and instead directing it to a sub-process utilizing the two step chemistry described in the patents listed above. The process selectively converts ethane to ethylene. The benefits are multiple:

1. By reducing the recycle to the furnace, additional fresh feed can be introduced, effectively increasing the capacity of the plant
2. By providing an extremely pure feed of ethylene, the sub-process reduces demand on the separations systems, again effectively increasing the capacity of the plant.
3. The purity of ethylene produced in the sub-process results in a substantial reduction in operating costs. For example, the conventional ethylene process produces, as a byproduct, acetylene, which must be hydrogenated selectively to ethylene, a difficult process. The production of ethylene described herein does not result in the production of acetylene thereby reducing the amount of acetylene produced in the ethylene facility.
4. The addition of the reactor allows the incremental expansion of an existing plant without the need for the large investment required for a new plant. Current ethylene technology is only cost effective on a huge scale, thus preventing the addition of small amounts of capacity when there is a small excess of demand. The ability to add to an existing location also capitalizes on the existing infrastructure, reducing the cost of the expansion.

In addition to the foregoing, it has been determined that the various metal oxides used in the metathesis reaction can also serve as adsorbents/reactants to control the release hydrogen halide or alkyl halides to the environment. Incorporating a metal oxide into a purge system within the plant not only controls the release of such compounds, but also serves as a means to recover bromine for further use in the process.

EXAMPLE III

Alkane halogenation

Ethane Bromination Reaction

A mixture of ethane and bromine of molar ratio 3.6:1 was created by passing an ethane stream (2.0 ml/minute) through a bromine bubbler which was held at 21.0° C. The mixture was passed into a reactor (glass tube ID 0.038", heating zone length 4"), which was heated to 400° C. The effluent was analyzed by GC and by NMR analysis of products trapped in deuterochloroform. 100% bromine conversion with 27.4% ethane conversion were obtained. The selectivity to ethylbromide was 89.9%. The other products were multiply brominated ethanes, the majority (>90% of the balance) being dibromoethanes.

Ethane Chlorination Reaction

A mixture of ethane and chlorine of molar ratio 2:1 (total flowrate 5 ml/min) is passed through a reactor (glass tube ID 0.038", heating zone length 4"), which is heated to 350° C. 100% chlorine conversion and 45% ethane conversion are obtained with ethylchloride selectivity of 90%.

Ethane Iodination Reaction

A mixture of ethane and iodine of molar ratio 1:4 (total flowrate 5 ml/min) is passed through a reactor (glass tube ID 0.38", heating zone length 4"), which is heated to 400° C. 10% ethane conversion is obtained with iodoethane selectivity of 85%.

Propane Bromination

A mixture of propane and bromine of molar ratio 3.6:1 was created by passing a propane stream (2.0 ml/minute) through a bromine bubbler which was held at 21.0° C. The mixture was passed into a reactor (glass tube ID 0.038", heating zone length 4"), which was heated to 350° C. The effluent was analyzed by GC and by NMR analysis of products trapped in deuterochloroform. 100% bromine conversion with 27% propane conversion were obtained. The selectivity to 2-bromopropane was 90%. The other products were 2,2-dibrompropane (~10%) and 1-bromopropane (<1%).

Higher Alkane Bromination

A mixture of alkane ($C_nH_{2n+2}$ 3<n<21) and bromine in a molar ratio of 5:1 are passed into a reactor (glass tube ID 0.038", heating zone length 4"), which is heated to 300° C. 100% bromine conversion is obtained with 18% alkane conversion and 90% selectivity to monobromoalkane.

Liquid-Phase Higher Alkane Bromination

Pressurized dodecane liquid is mixed with bromine in a 10:1 molar ratio. The mixture is passed through a tubular reactor held at 250° C. 100% bromine conversion is obtained with 90% selectivity to dodecylbromide.

Reproportionation of $C_2$ compounds:

100 mmol/hr of ethane and 100 mmol/hr of bromine are fed to a reactor containing a Pt/silica catalyst held at 400° C. A recycle stream of 46 mmol/hr ethane and 50 mmol/hr of multiply brominated ethanes is also fed to the reactor. Equilibrium is reached in the reactor with 100% bromine conversion and a product distribution of 46 mmol/hr ethane, 100 mmol/hr ethyl bromide and 50 mmol/hr higher bromides. 100 mol of HBr is also formed. The products are separated into 3 streams: (1) ethane/HBr, (2) ethyl bromide, and (3) higher bromides. Stream (1) is passed over a regenerable metal oxide, neutralizing the HBr and producing water. The water is separated out prior to recycling the ethane. Stream (3) is also recycled to the reactor.

Reproportionation of $C_2$ Compounds without Halide Addition:

100 mmol/hr of ethane and 10 mmol/hr dibromoethane are fed to a reactor containing a zirconia catalyst held at 300° C. A product distribution of 91 mmol/hr ethane 18 mmol/hr ethyl bromide and 1 mmol/hr dibromoethane is obtained.

Reproportionation of $C_{10}$ Compounds:

100 mmol/hr of decane and 100 mmol/hr of bromine are fed to a reactor containing a Rh/silica catalyst held at 300° C. A recycle stream of 100 mmol/hr decane and 80 mmol/hr of dibromodecane and more highly brominated decanes is also fed to the reactor. The reactor achieves 100% bromine conversion and a product distribution of 100 mmol/hr decane 100 mmol/hr decyl bromide and 80 mmol/hr multiplybrominated decane. 100 mol of HBr is also formed. The products are separated into 4 streams: (1) HBr (2) decane (3) decyl bromide, and (4) higher bromides. Stream (1) is passed over a regenerable metal oxide, neutralizing the HBr and producing water. Streams (2) and (4) are recycled to the reactor.

Reproportionation of $C_{10}$ Compounds without Bromine Addition:

100 mmol/hr of decane and 10 mmol/hr dibromodecanes (mixed isomers) are fed to a reactor containing a Rh/silica catalyst held at 200° C. A product distribution of 91 mmol/hr decane 18 mmol/hr decyl bromide and 1 mmol/hr dibromodecanes is obtained.

Reproportionation of Mixed $C_1$–$C_3$ Compounds:

A stream of dibromomethane (1 mmol/hr) and dibromoethane (2 mmol/hr) is combined with a stream of ethane (95 mmol/hr), methane (3 mmol/hr), and propane (2 mmol/hr) in a reactor containing Ru/silica which is held at 250° C. The product of the reactor are ethane (96 mmol/hr), methane (4 mmol/hr), ethyl bromide (1 mmol/hr), dibromopropane (2 mmol/hr), and other brominated products (trace).

EXAMPLE IV

Reactions of Alkyl Halides with Metal Oxides and Other Solids

Preparation of Zr Solution $Zr(OCH_2CH_2CH_3)_4$ (70 (w)% in isopropanol, 112.6 ml) was dissolved (under stirring) in a solution of 56.6 g oxalic acid in 200 ml of water. After stirring for 10 minutes, the solution was diluted with water to make a total volume of 500 ml. A solution with a Zr concentration of 0.5M was obtained.

Preparation of M1

$Co(NO_3)_2$ (0.5 M, 100.0 ml) was added to 100 ml of a stirring Zr solution (0.5M). After stirring for a few minutes, a gel was obtained. The gel was dried at 120° C. for 4 hours, then calcined at 500° C. for 4 hours. After grinding in a mortar and pestle, M1 was obtained.

Preparation of M2

$Fe(NO_3)_3$ (0.5 M, 50.0 ml) and $Zn(NO_3)_2$ (0.5 M, 50.0 ml) were added to 100 ml of a stirring Zr solution (0.5M). After stirring for a few minutes, a gel was obtained. The gel was dried at 120° C. for 4 hours, then calcined at 500° C. for 4 hours. After grinding in a mortar and pestle, M2 was obtained.

Preparation of M3

$Co(NO_3)_2$ (0.5 M, 80.0 ml) and boric acid (0.25 M, 40.0 ml) were added to 100 ml of a stirring Zr solution (0.5M). After stirring for a few minutes, a gel was obtained. The gel was dried at 120° C. for 4 hours, then calcined at 500° C. for 4 hours. After grinding in a mortar and pestle, M3 was obtained.

Preparation of M4

$Co(NO_3)_2$ (0.5 M, 80.0 ml) and $KNO_3$ (0.5 M, 20.0 ml) were added to 100 ml of a stirring Zr solution (0.5M). After stirring for a few minutes, a gel was obtained. The gel was dried at 120° C. for 4 hours, then calcined at 500° C. for 4 hours. After grinding in a mortar and pestle, M4 was obtained.

Preparation of M5

A slurry of chromatographic silica and cobalt nitrate sufficient to give a loading of 40 wt % $Co_3O_4$ was made. The slurry was calcined at 400° C. for 2 hr, yielding M5.

Bromination of Ethane and Reaction with M1:

A mixture of ethane and bromine of molar ratio 10:1 was created by passing an ethane stream (5 cc/min) through a bromine bubbler which was held at 0° C. The mixture was passed into a first reactor (glass tube ID 0.38", heating zone length 4"), which was heated to 350° C. The effluent was previously analyzed by GC and by NMR analysis of products trapped in deuterochloroform. 100% bromine conversion with 9.5% ethane conversion were obtained. The selectivity to bromoethane was greater than 94%. The effluent of the first reactor was passed into a second reactor (glass tube ID 0.38", heating zone length 4"), which was heated to various temperatures and which contained 5 g of M1 (except for the 350° C. run which used 1 g of M1). The respective brominated ethane conversions at 175° C., 200° C., 225° C., 250° C., and 350° C. were approximately 41%, 56%, 69%, 82%, and 90%, respectively. The ethylene selectivities (moles of ethylene/moles of all detected products) were approximately 1%, 7%, 20%, 34%, and 90% at 175° C., 200° C., 225° C., 250° C., 350° C. At 350° C., the product mix (excluding unreacted ethyl bromide) was 90% ethylene, 5% carbon dioxide, 4% vinyl bromide, and 1% other (largely acetone).

Reaction of Ethyl Bromide with M1:

Liquid ethyl bromide (0.6 ml/hr) was vaporized by combining with an inert nitrogen carrier gas. The mixture was passed through a reactor (glass tube ID 0.038", heating zone length 4") containing 2 g of metal oxide M1 which was heated to 350° C. The products were analyzed using GC. 100% ethyl bromide conversion was obtained for 5 hours. An ethylene selectivity of 96% was obtained. Byproducts included carbon dioxide (2%), ethanol (<1%), ethane (<0.5%).

Reaction of Ethyl Chloride with M1:

Ethyl chloride (1 ml/min) is passed through a reactor (glass tube ID 0.038", heating zone length 4") containing 5 g of metal oxide M1 which is heated to 350° C. 100% ethyl chloride conversion is obtained. An ethylene selectivity of 90% is obtained. M1 is regenerated by heating to 600° C. in oxygen with recovery of the chlorine.

Catalytic Reaction of Ethyl Bromide with Titania:

Liquid ethyl bromide (0.6 ml/min) was vaporized by combining with an inert nitrogen carrier gas. The mixture was passed a reactor (glass tube ID 0.38", heating zone length 4") containing 5 g of titania ($TiO_2$) which was heated to 275° C. The reaction products were passed through an aqueous sodium hydroxide trap to remove residual HBr prior to GC analysis. 60% ethyl bromide conversion was obtained with ethylene selectivity of >99% with no ethane observed within the detection limits of <100 ppm. In another configuration, the HBr is scrubbed with copper oxide, which can be regenerated, instead of sodium hydroxide.

Catalytic Reaction of Alkyl Bromide with Solid Catalyst:

A stream containing alkyl bromide ($C_nH_{2n+2}$ 1<n<21) or a mixture of alkyl bromides is passed over a solid catalyst consisting of cobalt bromide, titania, platinum on silica, or other suitable material between 250 and 350° C. 80% of the alkyl bromide is converted to olefin with 95% selectivity. The hydrogen bromide produced is reacted with copper oxide, producing copper bromide and water. The copper bromide is regenerated by flowing oxygen over it at 350° C., which liberates bromine, which is recovered.

Propane Bromination and Subsequent Reaction with M5:

A mixture of propane and bromine of molar ratio 3.6:1 was created by passing a propane stream (5.0 ml/minute) through a bromine bubbler which was held at 21.0° C. The mixture was passed into a first reactor (glass tube ID 0.038", heating zone length 4"), which was heated to 350° C. The effluent was previously analyzed by GC and by NMR analysis of products trapped in deuterochloroform. 100% bromine conversion with 27% propane conversion were obtained. The selectivity to 2-bromopropane was 90%. The other products were 2,2-dibrompropane (~10%) and 1-bromopropane (<1%). The effluent of the first reactor was passed into a second reactor (glass tube ID 0.38", heating zone length 4"), which was heated to 350° C. and hich contained 5 g of M5. The products were analyzed using GC. The selectivities (based on propane conversion) were propylene (90%), acetone (5%), other (5%).

Reaction of 1-Bromodecane with M3:

Liquid decylbromide (0.6 ml/min) was passed (with a nitrogen carrier gas) into a reactor (glass tube ID 0.38", heating zone length 4") containing 2 g of metal oxide M3 which was heated to 200° C. The sample of M3 used was previously used in more than 5 reaction/regeneration cycles. The reaction was run for 2 hours with the products collected in 6 g of cold $CDCl_3$. NMR analysis demonstrated 100% conversion, and the products were predominantly internal olefins with a selectivity of greater than 85%.

Reaction of 1-Bromopentane with M3:

Nitrogen (5 ml/min) was bubbled through 1-bromopentane at room temperature and fed to a reactor (glass tube ID 0.38", heating zone length 4") containing 2 g of metal oxide M3 which was heated to 200° C. The sample of M3 used was previously used in more than 5 reaction/regeneration cycles. The reaction was run for 2 hours with the products collected in 6 g of cold $CDCl_3$. NMR analysis demonstrated 100% conversion, and the products were predominantly internal olefins with a selectivity of greater than 90%.

Reaction of Mixed Alkyl Bromides with M1:

A stream containing a mixture of 90% alkyl bromides ($C_nH_{2n+1}Br$ 1<n<21), 9% dibromoalkanes ($C_nH_2Br_2$ 1<n<21), and 1% more highly brominated alkanes is passed over M1 at 250° C. 100% conversion is obtained with a product molar composition of 80% olefins, 8% diolefins, and a balance consisting of carbon dioxide, alcohols, glycols, and other hydrocarbons.

Reaction of Dibromododecane with M1:

Mixed isomers of dibromododecane are passed over a bed of M1 at 300° C. 100% conversion is obtained with 80% selectivity to diolefin.

Reaction of Vinyl Bromide with Copper Oxide:

A stream containing 10 mol % vinyl bromide is passed over cupric oxide at 350° C. More than 99.9% of the vinyl bromide is removed from the stream. The vinyl bromide reacts with the cupric oxide producing cuprous oxide, copper bromides, carbon dioxide, and water. Following reaction, the solid is annealed in oxygen at 375° C., liberating bromine for reuse and regenerating the cupric oxide.

Reaction of Mixed Bromides with Copper Oxide:

A stream containing a mixture of organic bromides is passed over cupric oxide at 350° C. More than 99.9% of the bromides are removed from the stream. The bromides react with the cupric oxide producing cuprous oxide, copper bromides, carbon dioxide, and water. Following reaction, the solid is annealed in oxygen at 375° C., liberating bromine for reuse and regenerating the cupric oxide.

Addition of Water to Ethane Reaction:

A mixture of ethane and bromine of molar ratio 10:1 was created by passing an ethane stream (5 ml/min) through a bromine bubbler which was held at 0° C. The mixture was passed into a first reactor (glass tube ID 0.038", heating zone length 4"), which was heated to 350° C. The effluent was previously analyzed by GC and by NMR analysis of products trapped in deuterochloroform. 100% bromine conversion with 9.5% ethane conversion were obtained. The selectivity to bromoethane was greater than 94%. The effluent of the first reaction was combined with the addition of variable amounts of excess water and passed into a second reactor (glass tube ID 0.38", heating zone length 4"), which contained 5 g of M1 at 200° C. As the water:bromine molar ratio was varied from 1 to 4 to 9, the ethanol produced increased from 0.07 to 0.09 to 0.14 mmol/hr respectively. The corresponding ether production rates were 0.21, 0.22, and 0.07.

Addition of Water to Higher Alkyl Bromide Reaction:

A mixture of steam and dodecylmonobromides in a molar ratio of 10:1 is fed to a bed of metal oxide M4 at 175° C. 100% of the dodecylmonobromide is converted with a selectivity of 50% to dodecylalcohols and 50% to dodecene (various isomers).

Simultaneous Steam Stripping of Higher Olefins:

A mixture of steam and dodecylmonobromides in a molar ratio of 10:1 is fed to a bed of metal oxide M1 at 250° C. 100% of the dodecylmonobromide is converted with a selectivity of 90% to dodecene (various isomers).

Post-Reaction Steam Stripping of Higher Olefins:

Dodecylmonobromides are fed to a bed of metal oxide M3 at 200° C. 100% of the dodecylmonobromide are converted with a selectivity of 80% to dodecene (various isomers). At the conclusion of the reaction, 10% of the product remains adsorbed to the solid and 95% of this is recovered by passing steam through the reactor at a flowrate equal to ten times the reactant flowrate for a period of 10 minutes.

Higher Olefin Hydration:

Dodecylmonobromides are fed to a bed of metal oxide M1 at 200° C. 100% of the dodecylmonobromide are converted with a selectivity of 90% to dodecene (various isomers) The product mixture is fed along with a ten fold excess of water to a bed of sulfated zirconia held at 175° C. 50% conversion of dodecene to dodecyl alcohols (mixed isomers) is achieved.

Neutralization of HBr from a Mixed Stream with Calcium Oxide and Subsequent Regeneration:

A stream containing hydrogen bromide, ethyl bromide, ethyl dibromide, and higher bromides of ethane is passed over calcium oxide at 150° C. The hydrogen bromide reacts with the oxide, producing calcium bromide and water. The organic bromides pass through the reactor substantially unreacted. The calcium bromide is subsequently oxidized by passing air over the material at 500° C., releasing bromine and regenerating the calcium oxide.

Neutralization of HBr from a Mixed Stream with M1 and Subsequent Regeneration:

A stream containing hydrogen bromide, ethyl bromide, ethyl dibromide, and higher bromides of ethane is passed over M1 at 150° C. The hydrogen bromide reacts with the oxide, producing cobalt bromide and water. The organic bromides pass through the reactor substantially unreacted. The cobalt bromide is subsequently oxidized by passing oxygen over the material at 350° C., releasing bromine and regenerating M1.

Neutralization of HBr with M1 and Subsequent Regeneration:

A stream of hydrogen bromide is passed over M1 at 150° C. The hydrogen bromide reacts with the oxide, producing cobalt bromide and water. The cobalt bromide is subsequently oxidized by passing oxygen over the material at 350° C., releasing bromine and regenerating M1.

Reaction with Oxybromide:

Ethyl bromide is passed over bismuth oxybromide at 350° C. 80% of the ethylbromide is converted with a selectivity to ethylene of 80%. In the course of the reaction, the bismuth oxybromide is converted to bismuth bromide, which is subsequently reacted with oxygen at 500° C., releasing a portion of the bromine in the solid and regenerating the bismuth oxybromide.

Reaction with Hydroxide and Hydrate:

Steam is passed over M1 at 200° C., resulting in the formation of cobalt hydroxide and cobalt oxide hydrate, supported on zirconia. Ethyl bromide is passed over this material at 200° C. 50% of the ethyl bromide is converted, with 80% selectivity to ethanol. Following reaction, the cobalt bromide is oxidized to cobalt oxide by passing oxygen through the solid, liberating bromine. The oxide is then exposed to steam to regenerate the hydroxide and hydrate.

Regeneration of M1:

A mixture of ethane and bromine of molar ratio 10:1 was created by passing a pressurized ethane stream through a bromine bubbler which was held at 7° C. The mixture was passed into a first reactor (glass tube ID 0.38", heating zone length 4"), which was heated to 350° C. The effluent was previously analyzed by GC and by NMR analysis of products trapped in deuterochloroform. 100% bromine conversion with 9.5% ethane conversion were obtained. The selectivity to bromoethane was greater than 94%. The effluent of the first reactor (approximately 4 cc/min) was passed into a second reactor (glass tube ID 0.38", heating zone length 4"), which was heated to 200° C. and which contained 5 g of M1. The products were analyzed using GC. After 5 hours of reaction, the reactors were purged and the solid was regenerated at 350° C. with flowing oxygen until bromine evolution ceased. After 26 reaction/regeneration cycles, the material remained active and the chemical performance (conversion, selectivity) remained unchanged within experimental error.

Regeneration of M2:

A mixture of ethane and bromine of molar ratio 10:1 was created by passing an ethane stream through a bromine bubbler which was held at 0° C. The mixture was passed into a first reactor (glass tube ID 0.38", heating zone length 4"), which was heated to 350° C. The effluent was previously analyzed by GC and by NMR analysis of products trapped in deuterochloroform. 100% bromine conversion with 9.5% ethane conversion were obtained. The selectivity to bromoethane was greater than 94%. The effluent of the first reactor (approximately 4 cc/min) was passed into a second reactor (glass tube ID 0.38", heating zone length 4"), which was heated to 200° C. and which contained 5 g of M2. The products were analyzed using GC. After 5 hours of reaction, the reactors were purged and the solid was regenerated at 350° C. with flowing oxygen until bromine evolution ceased. The bromine was trapped in an aqueous sodium hydroxide trap and was analyzed using UV/VIS spectroscopy. For four sequential runs, the bromine recovery was determined to be 94, 108, 100, and 98% of the bromine input, with an uncertainty of approximately 5%. The chemical performance of the M2 was unchanged over these runs.

Although preferred embodiments of the invention have been illustrated in the accompanying Drawings and described in the foregoing Detailed Description, it will be understood that the invention is not limited to the embodiments disclosed but is capable of numerous rearrangements, modifications, and substitutions of parts and elements without departing from the spirit of the invention.

The invention claimed is:

1. A method of synthesizing olefins, alcohols, ethers, and aldehydes comprising the steps of:
    providing a first reactant selected from the group consisting of alkanes, alkenes, alkynes, dienes, and aromatics;
    providing a second reactant comprising a halide selected from the group consisting of chlorine, bromine and iodine;
    reacting the first reactant and the second reactant to form a first reaction product;
    reacting the first reaction product with a solid oxidizer thereby forming a product selected from the group consisting of olefins, alcohols, ethers, and aldehydes, and spent oxidizer;
    oxidizing the spent oxidizer to produce the original solid oxidizer and the original second reactant;
    recycling the solid oxidizer; and
    recycling the second reactant.

2. The method according to claim 1 wherein the first reactant comprises an alkane having a carbon number $\leq 16$.

3. The method according to claim 1 wherein the solid oxidizer comprises a metal oxide.

4. The method according to claim 1 wherein the solid oxidizer comprises a metal halide.

5. The method according to claim 1 wherein the solid oxidizer comprises a solid hydrate.

6. The method according to claim 5 wherein the solid hydrate comprises a metal oxyhydrate.

7. The method according to claim 5 wherein the solid oxidizer comprises a solid hydrate selected from the group consisting of hydrates of halides, sulfides, carbonates, phosphates, phosphides, nitrides, and nitrates.

8. The method according to claim 1 wherein the step of reacting the first reaction product with a solid oxidizer is carried out at a temperature of between about 350° C. and about 400° C.

9. The method according to claim 1 wherein the solid oxidizer is selected from the group consisting of MgO, CaO, $FeMoO_x$, $FeWO_x$, $La_2O_3$, $Ca(OH)_2$, $PbO$, $CuO$, $Bi_2O_3$, $MgZrO_x$, ZnO.

10. The method according to claim 1 wherein the solid oxidizer comprises $CoZrO_x$.

11. The method according to claim 1 including the additional step of including water in the reaction between the first reaction product and the solid oxidizer.

12. A method of synthesizing olefins, alcohols, ethers, and aldehydes comprising the steps of:
    providing a first reactant selected from the group consisting of alkanes, alkenes, alkynes, dienes, and aromatics;
    providing a second reactant comprising bromine;
    reacting the first reactant and the second reactant to form a first reaction product;
    reacting the first reaction product with a solid oxidizer comprising $CoZrO_x$ thereby forming a product selected from the group consisting of olefins, alcohols, ethers, and aldehydes, and spent oxidizer;
    oxidizing the spent oxidizer to produce the original solid oxidizer and the original second reactant;
    recycling the solid oxidizer; and
    recycling the second reactant.

13. The method according to claim 12 wherein the first reactant comprises an alkane having a carbon number $\leq 16$.

14. The method according to claim 12 wherein the step of reacting the first reaction product with a solid oxidizer is carried out at a temperature of between about 350° C. and about 400° C.

15. The method according to claim 12 including the additional step of including water in the reaction between the first reaction product and the solid oxidizer.

16. A method of synthesizing olefins comprising the steps of:
    providing an alkane stream comprising by-products resulting from the manufacture of olefins;
    providing a second reactant comprising a halide selected from the group consisting of chlorine, bromine and iodine;
    reacting the alkane stream and the second reactant to form first reaction products and hydrogen halide;
    separating the first reaction products from the hydrogen halide;
    reacting the first reaction products with a solid oxidizer thereby forming a stream of olefins and spent oxidizer;
    oxidizing the spent oxidizer resulting from oxidation of the first reaction products to produce the original solid oxidizer and the original second reactant;
    recycling the solid oxidizer;
    recycling the second reactant;
    reacting the hydrogen halide with a solid oxidizer thereby forming water and spent oxidizer;
    oxidizing the spent oxidizer resulting from the oxidation of the hydrogen halide to produce the original solid oxidizer; and
    recycling the solid oxidizer.

17. The method according to claim 16 wherein the alkanes comprising the alkane stream have carbon numbers $\leq 16$.

18. The method according to claim 16 wherein the solid oxidizer comprises a metal oxide.

19. The method according to claim 16 wherein the solid oxidizer comprises a metal halide.

20. The method according to claim 16 wherein the solid oxidizer comprises a solid hydrate.

21. The method according to claim 20 wherein the solid hydrate comprises a metal oxyhydrate.

22. The method according to claim 20 wherein the solid oxidizer comprises a solid hydrate selected from the group consisting of hydrates of halides, sulfides, carbonates, phosphates, phosphides, nitrides, and nitrates.

23. The method according to claim 16 wherein the step of reacting the first reaction product with a solid oxidizer is carried out at a temperature of between about 350° C. and about 400° C.

24. The method according to claim 16 wherein the solid oxidizer is selected from the group consisting of MgO, CaO, $FeMoO_x$, $FeWO_x$, $La_2O_3$, $Ca(OH)_2$, PbO, CuO, $Bi_2O_3$, $MgZrO_x$, ZnO.

25. The method according to claim 16 wherein the solid oxidizer comprises $CoZrO_x$.

26. The method according to claim 16 including the additional step of including water in the reaction between the first reaction product and the solid oxidizer.

\* \* \* \* \*